United States Patent
Perl

(10) Patent No.: US 10,104,919 B2
(45) Date of Patent: Oct. 23, 2018

(54) BRA LINING

(71) Applicant: Avigail Perl, Tel Aviv (IL)

(72) Inventor: Avigail Perl, Tel Aviv (IL)

( * ) Notice: Subject to any disclaimer, the term of this patent is extended or adjusted under 35 U.S.C. 154(b) by 234 days.

(21) Appl. No.: 14/371,507

(22) PCT Filed: Jul. 10, 2013

(86) PCT No.: PCT/IL2013/050590
§ 371 (c)(1),
(2) Date: Jul. 10, 2014

(87) PCT Pub. No.: WO2014/009956
PCT Pub. Date: Jan. 16, 2014

(65) Prior Publication Data
US 2015/0150310 A1    Jun. 4, 2015

Related U.S. Application Data

(60) Provisional application No. 61/669,689, filed on Jul. 10, 2012.

(51) Int. Cl.
| | | |
|---|---|---|
| A41C 3/12 | (2006.01) | |
| A41D 27/12 | (2006.01) | |
| A61F 13/14 | (2006.01) | |
| A61F 13/15 | (2006.01) | |

(52) U.S. Cl.
CPC ............. *A41C 3/12* (2013.01); *A41D 27/12* (2013.01); *A41B 2300/24* (2013.01); *A61F 13/14* (2013.01); *A61F 2013/15016* (2013.01)

(58) Field of Classification Search
CPC .......... A41C 3/065; A61F 13/15; A61F 2013/15016; A61F 13/14; A41D 27/12; A41B 2300/24
USPC ............ 450/93, 37, 54–57, 60, 81, 39; 604/385.07, 358
See application file for complete search history.

(56) References Cited

U.S. PATENT DOCUMENTS

| | | | |
|---|---|---|---|
| 5,858,014 A | 1/1999 | Kepes et al. | |
| 6,264,530 B1 | 7/2001 | Cosentino | |
| 7,467,987 B2 * | 12/2008 | Khalaf .............. | A41C 3/0064 424/402 |

(Continued)

FOREIGN PATENT DOCUMENTS

| | | |
|---|---|---|
| JP | 07300702 A  * | 11/1995 |
| JP | 2004-332143 | 11/2004 |
| WO | 2010/047986 | 4/2010 |

OTHER PUBLICATIONS

International Search Report for PCT/IL2013/050590 dated Nov. 14, 2013.

(Continued)

*Primary Examiner* — Khaled Annis
*Assistant Examiner* — Brieanna Szafran
(74) *Attorney, Agent, or Firm* — Marc Van Dyke; Fourth Dimension IP

(57) ABSTRACT

The current invention aims to absorb sweat and body odor from the breasts. It also protects the skin by providing a cushioned support strip below the bra wire. The invention is a lining to be affixed between the inner lining of a brassiere and the skin, having three layers and a set of flaps protruding from the device adapted to be folded outward to hold the device in place.

9 Claims, 3 Drawing Sheets

(56) References Cited

U.S. PATENT DOCUMENTS

| | | | |
|---|---|---|---|
| 7,905,763 B1* | 3/2011 | Frank | A41D 27/12 |
| | | | 450/37 |
| 2006/0020234 A1* | 1/2006 | Chou | A61F 13/00063 |
| | | | 602/41 |
| 2008/0004588 A1 | 1/2008 | Gavitt | |
| 2008/0294136 A1* | 11/2008 | Kawakami | A61F 13/141 |
| | | | 604/385.07 |
| 2010/0022164 A1 | 1/2010 | Taylor | |
| 2010/0105286 A1* | 4/2010 | Frye | A61F 13/145 |
| | | | 450/57 |
| 2012/0157951 A1 | 6/2012 | Johnson | |
| 2014/0302745 A1* | 10/2014 | Golubovic | A61F 13/15 |
| | | | 450/1 |
| 2017/0013887 A1* | 1/2017 | Lilien | A61F 13/145 |

OTHER PUBLICATIONS

Office Action dated Nov. 23, 2015 in corresponding European Application No. 13817130.1.

* cited by examiner

BRA LINING

This application claims benefit of U.S. Provisional Patent Application 61/669,689 filed Jul. 10, 2012.

FIELD OF THE INVENTION

The present invention relates to a brassiere lining and, more particularly, to a hygienic product for protecting the skin below the breast while wearing.

BACKGROUND OF THE INVENTION

Brassieres, commonly known as bras, are undergarments made to support a woman's breasts. The cup of the bra is designed to contain the breast. The cup often contains stiffening panels to support the breasts, and the edge of the cup is generally a rib-like, tough material, often containing an underwire to raise the breasts and prevent sagging. Bra wearers complain of rubbing around the cup, sweatiness in the under-bra area, and general itching resulting in many cases in rashes and irritated skin. Consequently, there is a need for a product that keeps the wearer dry and comfortable, and complements wearing a bra.

Furthermore, the bra is an expensive item of clothing. Most women only own a few at a time. The bra often does not last long in its original state, losing color quickly and falling apart at the seams after several washes. Consequently, there is a need for a method of prolonging the useful life of a bra by enabling a woman to wear a bra for longer periods of time between washes.

U.S. Pat. No. 8,246,416 B2 describes a foldable one-piece insert worn between the bra and the body having irritation reducing and/or absorbent material portions which line the bra cup and that lie under the supported breast, and portions which extends toward the torso rear under the bra side straps and a portion extending below the bra line along the torso. Said invention includes straps which wrap around the wearer's torso in order to keep the invention in place. Additionally, said invention provides a simple solution to irritation caused by the metallic straps at the bottom of the bra.

U.S. Pat. No. 6,464,717 B1 describes a bra with hot/cold inserts for a therapeutic device in the form of a vest-like elastic garment adapted to be worn on the human upper torso. The device includes front panels having pockets therein for retaining gel packs. The device is effective in providing warm or cold therapy to the chest and rib areas. The garment can be used by humans of both genders. This invention is limited to therapeutic use.

U.S. Pat. No. 5,690,536 A describes a disposable bra liner comprising three cup-shaped coextensive layers attached together, with each layer presenting a circular periphery. The bra liners further include a structural member attached to the layers for maintaining the shape of the pad. The structural member includes an elastic band attached to the layers at their peripheries and preferably has a plurality of V-shaped folding portions. The invention does not deal with irritation caused by the metal underwire. Furthermore, the invention is held in place with the V shaped flaps (which therefore must be folded over), which does not offer the option of folding or unfolding the V-shaped folding portions, pursuant to the wearer's choice.

US 20120157951 A1 describes a bra liner which has a first sheet of fluid-pervious non-woven material having a first edge and a second edge. A second sheet of fluid pervious non-woven material having a first edge and a second edge is positioned in adjacent relationship to the first sheet. The first edge of the second sheet is joined to the first edge of the first sheet and the second edge of the second sheet is joined to the second edge of the first sheet. A breathable compartment is formed between the first and second sheets. A layer of super absorbent gel material and cotton fluff is positioned in the compartment. Said invention does not deal with irritation caused by the bra's metal underwire.

SUMMARY OF THE INVENTION

The current invention aims to absorb sweat and body odor in the upper body region in a similar way to the way a sanitary pad absorbs bodily fluid in the lower body of a woman. It also protects the skin by providing a cushioned support strip below the bra wire.

The bra lining provides a solution for any type of bra, including bras of the "push up", "sheer", and "sports" variety. The current invention provides a cheap, disposable, hygienic, thin, and lightweight solution.

The present invention relates to a lining to be affixed between a brassiere and the skin, comprising:
1. A first protective nylon (or any other non-woven material) protective material layer that is water proof that attaches to the bra with an adhesive.
2. A second middle thin absorbent layer, either with or without absorbing and perfuming substances. For example, the absorbent layer may comprise talcum powder to absorb sweat, odor, and bodily fluids.
3. A third smooth inner layer of cotton (or any other comfortable material) that is pressed against the skin.
4. Two bottom flexible flaps protruding from the lining. Said bottom flexible flaps are made of a comfortable and flexible material with the ability to fold around the bottom of the bra and attach to the outer side of the bra, protecting the skin from chafing and irritation caused by the underwire. Folding of the two flaps folds at least a portion of these two flaps such that a portion of the bottom of the lining separating the two flaps remains unfolded.
5. Wherein, a single lining supports both breasts.

Two top flexible flaps protruding from the lining. Said top flexible flaps are to fold diagonally around the top of the bra and attached to the outer side of the bra, creating a V-shape, to the wearer's choosing.

The lining is three dimensional, meaning not flat, rather it is rounded and possesses volume (similar to a bra cup) in order to fit perfectly into the bra with the adhesive side pressed against the bra, while the cotton side is pressed against the skin.

The present invention shall additionally be made of relatively cheap, disposable materials.

BRIEF DESCRIPTION OF THE DRAWINGS

Various embodiments are herein described, by way of example only, with reference to the accompanying drawings, wherein.

DESCRIPTION OF THE PREFERRED EMBODIMENTS

The following description is provided, alongside all chapters of the present invention, so as to enable any person skilled in the art to make use of said invention and sets forth the best modes contemplated by the inventor of carrying out this invention. Various modifications, however, will remain apparent to those skilled in the art, since the generic principles of the present invention may produce one or several other embodiments. The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

The principles and operation of a bra lining according to the present invention may be better understood with reference to the drawings and the accompanying description.

Figure 1:
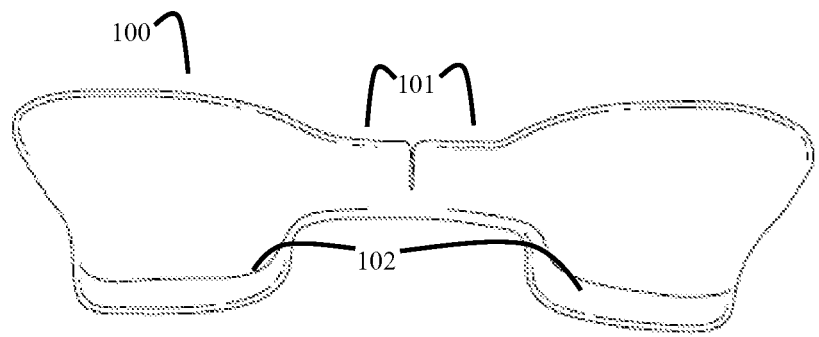
FIG. 1 is an obverse view of the bra lining with top flaps unfolded.

FIG. 1 shows the bra lining 100 with top flexible flaps 101 unfolded and bottom flexible flaps 102 unfolded. The linings come ready pressed out in the shape of a cup to fit into a three-dimensional cup of a bra. There are two bottom flaps 102 and two top flaps 101. The bottom flaps 102 folds around the bottom of the bra and attach to the outer side of the bra.

The central regions are top flaps. The top flap folds over the bra in the cleavage section. Both flaps are cushioned and give added protection from the underwire and help secure the bra lining, although the flaps do not necessarily have to be folded over. The top flap can either be left closed, or may be opened in the middle and folded outwards for lower cleavage.

Figure 2:
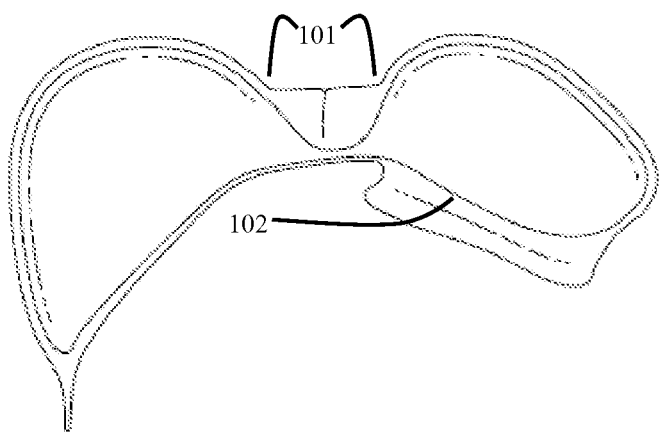
FIG. 2 is an obverse view of the bra lining with top flaps folded.

FIG. 2 shows the bra lining with top flaps 101 folded, the left bottom flap folded, and right bottom flap 102 unfolded.

Figure 3:
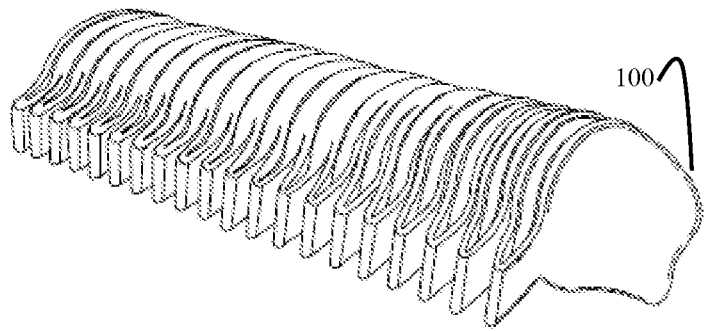
FIG. 3 is an isometric view of a set of stacked bra linings.

FIG. 3 is an isometric view of a set of stacked bra linings 100.

Figure 4:
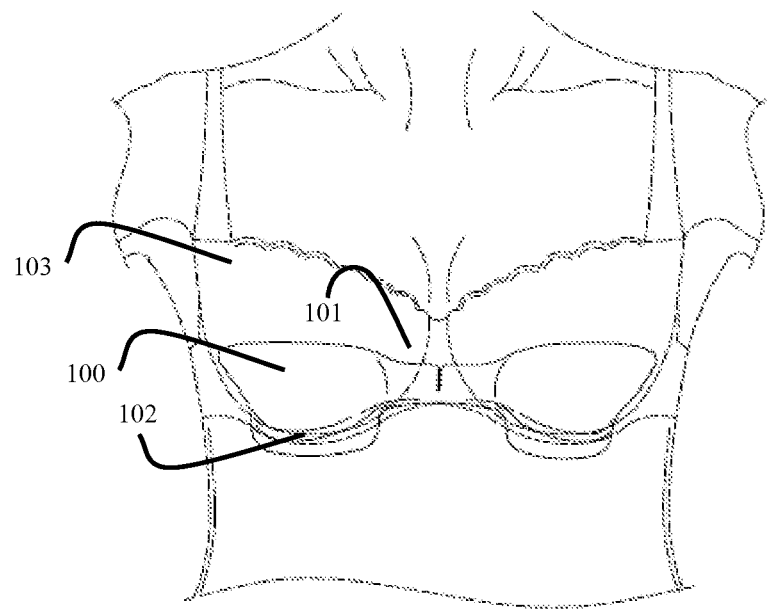
FIG. 4 is a front 'x-ray' view of a bra lining in use between bra and breasts, with bottom flaps unfolded.

FIG. 4 is a front 'x-ray' view of a bra lining 100 in use between bra 103 and breasts. Here the bottom flaps 102 and top flaps 101 are both in their unfolded state. FIG. 4 further depicts a slit 104 located largely in the middle of the lining. As can be seen, this embodiment further comprises 2 cups 105-106.

Figure 5:
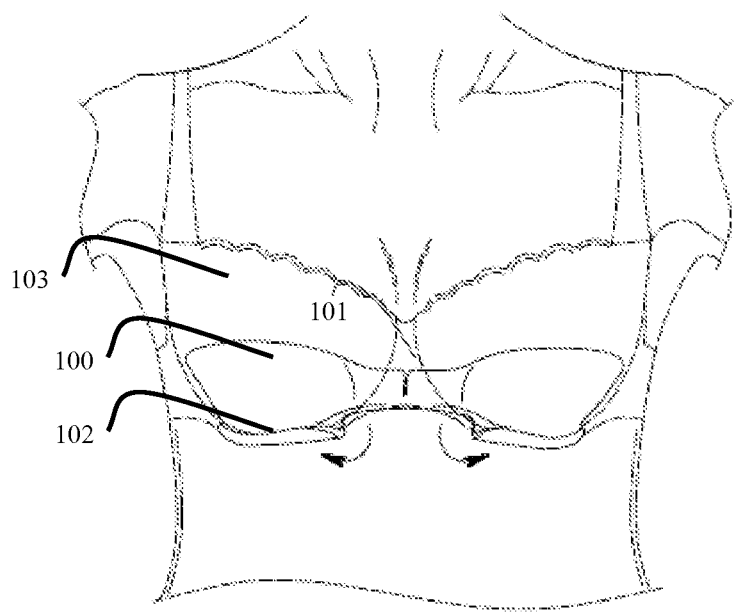
FIG. 5 is a front 'x-ray' view of a bra lining in use between bra and breasts, with bottom flaps folded underneath the bottom of the bra.

FIG. 5 is a front 'x-ray' view of a bra lining 100 in use between bra 103 and breasts, with bottom flaps 102 folded underneath the bottom of the bra and attached to the outer side thereof, and top flaps 101 still unfolded.

Figure 6:
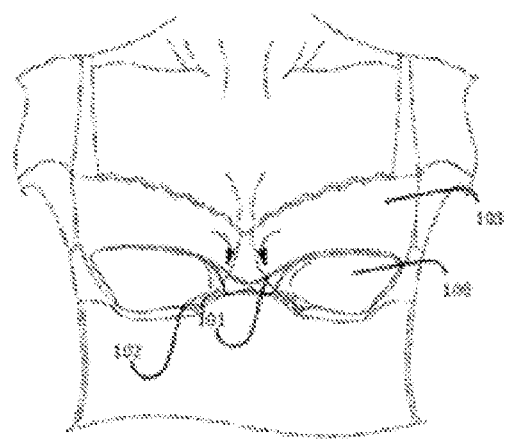
FIG. 6 is a front 'x-ray' view of a bra lining in use between bra and breasts, with bottom flaps folded underneath the bottom of the bra.

FIG. 6 is a front 'x-ray' view of a bra lining 100 in use between bra 103 and breasts, with bottom flaps 102 folded underneath the bottom of the bra and top flaps 101 folded.

Figure 7:
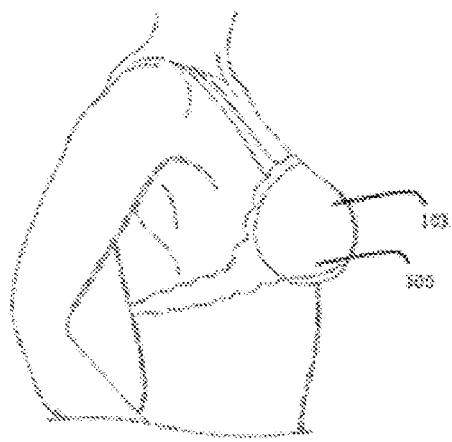
FIG. 7 is a side view of a bra lining in use between bra and breasts.

FIG. 7 is a side view of the bra lining 100 in use, showing its position relative to the bra 103.

Figure 8:
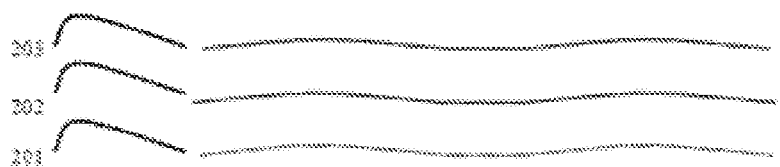
FIG. 8 is a cross-section view of the lining's layers.

Referring to FIG. 8, the bra lining comprises three layers in preferred embodiments. The first layer 201 is a generally a waterproof layer made of nylon or other synthetic fabric. The first layer makes contact with the bra and prevents any fluids and odors from penetrating the fabric of the bra. The first layer may contain adhesive for affixing to the inside of the bra. The second middle layer 202 is an absorbent layer for absorbing sweat and body fluids. The second layer may optionally contain scented talcum powder that is scented with, for example, a feminine scent. As another example, baby powder may be employed. Moisture is retained inside this second layer of the bra lining. The third layer 203 is a soft layer that comes into contact with the skin. This third layer is made up of a cotton-based material that provides cushioning.

The bra linings come in various sizes and colors.

The bra linings are thin and lightweight, and stretch to some extent. The bra linings do not add appreciable width or volume to the wearer's breasts. The bra linings have smooth, rounded edges for comfort. The bra linings are disposable and individually wrapped.

Improvements and Add-Ons:

Aside from protecting the skin below the breast, absorbing sweat, elongating the bra life, and keeping the area fresh, dry and clean, the lining can also serve as a protection layer for women who have gone through breast augmentation through the crease below the breast. A scar tissue can form post-surgery at this location, and the lining can act as a soft shield which protects the scar from the hard wire inside the bra that rests on the tender scar tissue.

A short summary of the main innovative features of the inventive bra lining follows:

1. The whole linings is disposable.
2. The linings absorbs sweat, leaving the breast dry.
3. The linings protects the delicate skin in the area (and thus avoid rashes).
4. Leaves a light baby-powder scent (in some embodiments).
5. The linings is shaped in such a way that it curves perfectly onto the breast.
6. The linings elongates the life of any bra; since less laundering (a process known to ruin bras) is needed due to decreased sweat into the bra, the bras last longer.
7. The layer that rests on the breast has pores that funnel the sweat into the second (middle) layer. These pores are one way and so the sweat cannot travel back onto the skin.
8. The lining can serve as a protective layer between bra and scar tissue present in many post breast augmentation surgeries.
9. The whole lining is extremely thin, and its outer layer fabric is based on cotton. Therefore it is comfortable and will barely be noticeable for the woman wearing it.
10. The lining can be worn with any type of bra—regular straps, strapless, with or without wires, and with a sports bra.

While the invention has been described with respect to a limited number of embodiments, it will be appreciated that many variations, modifications and other applications of the invention may be made. Furthermore just as every particular reference may embody particular methods/systems, yet not require such, ultimately such teaching is meant for all expressions notwithstanding the use of particular embodiments. Therefore, the claimed invention as recited is not limited to the embodiments described herein.

The invention claimed is:

1. A method for absorbing moisture in bras comprising the steps of:
   a. attaching a lining to an inner side of a bra, said lining comprising:
      i. a first material layer;

ii. a second absorbent layer, attached to said first material layer and adapted to absorb bodily fluids;

iii. a material-based third layer attached to said second absorbent layer and adapted to engage skin of a user's breasts when said bra is worn; and iv. two bottom flexible flaps protruding from a bottom of the lining;

b. folding at least a portion of said bottom flexible flaps around a bottom edge of the bra; and c. attaching said bottom flexible flaps to an outer surface of first and second cups of the bra such that a portion of each of the first and the second cups of the bra is sandwiched between a respective portion of the lining and one of the bottom flexible flaps, wherein said attaching said lining comprises fitting said lining in said bra such that the lining spans both the first and the second cups of said bra and wherein, when said bra is worn by said user, the skin of the breasts of the user is protected from chafing and irritation.

2. The method of claim 1, wherein the lining further comprises two top flexible flaps, and the method further comprises folding said top flexible flaps over an upper edge of the bra and attaching said top flexible flaps to an outer side of the bra.

3. The method of claim 1 wherein said second absorbent layer comprises absorbent powder.

4. The method of claim 3 wherein said absorbent powder comprises talcum powder.

5. The method of claim 1 wherein said second absorbent layer comprises odorant.

6. The method of claim 1 wherein said lining is shaped so as to fit snugly within the first and the second cups of said bra.

7. The method of claim 1 wherein said material-based third layer comprises one-way pores such that sweat absorbed from the skin cannot travel back onto the skin.

8. The method of claim 1, wherein said folding comprises folding said at least a portion of said bottom flexible flaps such that a portion of said bottom of said lining separating said flaps remains unfolded.

9. A lining to be placed between an inner surface of a bra and skin of a user's breasts, said lining comprising:

a) a first layer that attaches to the inner surface of the bra with an adhesive;

b) a second layer adapted to come into contact with the skin of the user's breasts;

c) two bottom flexible flaps protruding from the lining and adapted, when said lining is attached to said inner surface of the bra, to be folded round a bottom edge of the bra and to attach to an outer surface of first and second cups of the bra; and d) a slit formed in an upper portion of said lining and centered therein, said slit defining two top flexible flaps protruding from the lining, said top flexible flaps being adapted to fold over an upper edge of the bra;

wherein said lining is adapted to span both the first and the second cups of the bra.

\* \* \* \* \*